(12) United States Patent
Suda et al.

(10) Patent No.: US 8,318,865 B2
(45) Date of Patent: Nov. 27, 2012

(54) EYE LENS MATERIAL AND METHOD OF MANUFACTURING THEREOF

(75) Inventors: Yukimitsu Suda, Yokohama (JP); Kazuyuki Miyazawa, Yokohama (JP); Kazuhiko Ishihara, Mitaka (JP)

(73) Assignees: Shiseido Company, Ltd., Tokyo (JP); Kazuhiko Ishihara, Tokyo (JP)

( * ) Notice: Subject to any disclaimer, the term of this patent is extended or adjusted under 35 U.S.C. 154(b) by 743 days.

(21) Appl. No.: 10/593,682

(22) PCT Filed: May 18, 2005

(86) PCT No.: PCT/JP2005/009082
§ 371 (c)(1),
(2), (4) Date: Aug. 18, 2008

(87) PCT Pub. No.: WO2005/114304
PCT Pub. Date: Dec. 1, 2005

(65) Prior Publication Data
US 2008/0300369 A1    Dec. 4, 2008

(30) Foreign Application Priority Data

May 24, 2004  (JP) .................................. 2004-153256
May 10, 2005  (JP) .................................. 2005-136845

(51) Int. Cl.
*C08C 19/24* (2006.01)
(52) U.S. Cl. .................. 525/340; 525/328.2; 525/328.8; 525/329.7; 525/330.4; 525/452; 525/459; 536/55.1; 536/56; 536/58; 536/85
(58) Field of Classification Search ............... 525/328.2, 525/328.8, 329.7, 330.4, 340, 452, 459; 536/55.1, 536/56, 58, 85
See application file for complete search history.

(56) References Cited

U.S. PATENT DOCUMENTS

| | | | | |
|---|---|---|---|---|
| 5,422,402 A | * | 6/1995 | Bowers et al. ............. | 525/328.2 |
| 6,075,066 A | * | 6/2000 | Matsuda et al. ............. | 523/106 |
| 6,213,604 B1 | * | 4/2001 | Valint et al. ................... | 351/177 |

FOREIGN PATENT DOCUMENTS

| | | |
|---|---|---|
| JP | 5-505121 | 8/1993 |
| JP | 10-177152 | 6/1998 |
| JP | 2000-111847 | 4/2000 |
| JP | 2000-169526 | 6/2000 |
| JP | 2001-337298 | 12/2001 |
| WO | 91/13639 A1 | 9/1991 |

OTHER PUBLICATIONS

"The analytical method for deposits on soft contact lenses", 2004, 4 pages, Material Stage, vol. 4, No. 1., pp. 73-79.

* cited by examiner

*Primary Examiner* — David W Wu
*Assistant Examiner* — Robert Jones

(57) ABSTRACT

The present invention is a method of manufacturing an eye lens material having a process in which a phosphorylcholine group-containing chemical compound represented by the following formula (1) is reacted and covalently bonded to the surface of an eye lens material having hydroxyl groups wherein the chemical compound represented by the following formula (2) is reacted and covalently bonded through ester-bonding to the eye lens material in an organic solvent.

The object of the present invention is to provide an eye lens material that prevents protein adsorption and a method of manufacturing thereof.

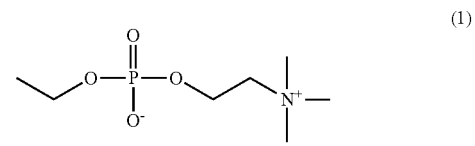

(1)

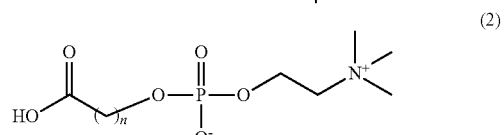

(2)

n denotes a natural number 1-18.

2 Claims, 1 Drawing Sheet

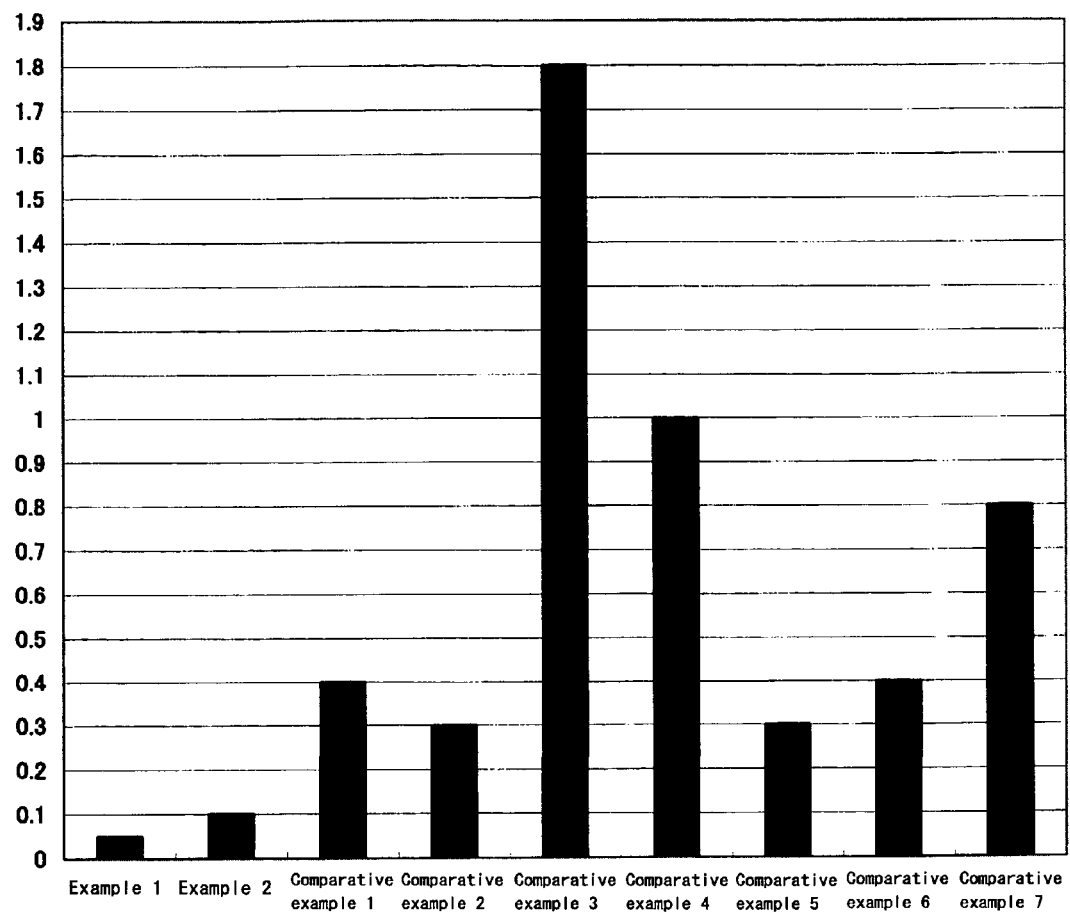

EYE LENS MATERIAL AND METHOD OF MANUFACTURING THEREOF

TECHNICAL FIELD

The present invention relates to an eye lens material for contact lenses and such, a method of manufacturing it, and a method of preventing protein adsorption. More specifically, it relates to a method of preventing protein stains by treating the surface of an eye lens material (particularly for contact lenses) by means of an after-treatment using a new phosphorylcholine group-containing chemical compound.

BACKGROUND ART

A practice of polymerizing phosphorylcholine group-containing monomers for use as a contact lens material is a prior art (Patent Documents 1-3). For example, Patent Document 1 discloses a moist soft contact lens containing a phosphorylcholine group-containing (meth)acrylic ester as a constitutional unit; it is described as having superior moisture content, oxygen permeability, and tensile strength, as well as reduced protein adsorption and the ability to suppress stain adhesion.

As an example of an after-treatment method for contact lenses, Patent Document 4 describes polymerization of phosphorylcholine group-containing monomers on the contact lens surface to prepare a contact lens having hydrophilic surfaces and reduced protein adsorption.

In addition, Patent Document 5 describes a reduction in protein adsorption by chemically bonding a low molecular weight phosphorylcholine carboxyl compound onto the contact lens surface.

That is, in Patent Document 5, formula (V) in the lower right column of page 5 and reaction formula 6 in the lower right column of page 6 describe a chemical structure formula of a phosphorylcholine carboxyl derivative that has been turned into an active ester. However, no description of the synthesis method or Examples is given and therefore this experiment cannot be reproduced: it cannot be called a disclosure of an invention. If said compound, a phosphorylcholine carboxyl derivative having the structure described, were to be synthesized based on ordinary organic chemistry commonsense, the method would be very cumbersome and the yield would be low, indicating very little practical use. Example 5 in the upper left column of page 9 describes a method of introducing phosphorylcholine groups onto the surface of a contact lens composed of a 4-hydroxyethyl methacrylate copolymer by treating glycerophosphorylcholine with 1,1'-carbonyldiimidazole. However, the target phosphorylcholine-treated contact lens could not be obtained as a result of an attempt to duplicate the Example described above.

Stains on a contact lens result from adsorption of proteins and/or lipids contained in lacrimal fluid; these stains can cause eye troubles such as allergies and infections (Non-patent Document 1). Protein stains cause a fatal problem particularly for a moist contact lens whose main ingredient is a 2-hydroxyethyl methacrylate polymer, a highly moist soft contact lens prepared by copolymerizing this with methacrylic acid, which is an ionic monomer, and a soft contact lens whose main ingredient is a polymer of a hydrophilic monomer such as N-vinyl pyrrolidone and N,N-dimethyl acrylamide.

Patent Document 1: Japanese Patent Laid-Open H10-177152 bulletin
Patent Document 2: Japanese Patent Laid-Open 2000-111847 bulletin
Patent Document 3: Japanese Patent Laid-Open 2000-169526 bulletin
Patent Document 4: Japanese Patent Laid-Open 2001-337298 bulletin
Patent Document 5: Japanese Patent Laid-Open H5-505121 bulletin
Non-patent Document 1: "Stains on soft contact lenses and analysis thereof", Material Stage, Vol. 4, No. 1, 2004

DISCLOSURE OF INVENTION

Problem that the Present Invention Aims to Solve

The present invention provides a contact lens that prevents protein stains by suppressing protein adsorption on the contact lens by means of an after-treatment in which phosphorylcholine groups are directly and covalently bonded onto the contact lens surface.

That is, the present invention does not prepare a protein adsorption prevention contact lens by polymerizing monomers having phosphorylcholine groups, as in methods described in Patent Documents 1-3 above; its object is to give contact lenses a superior protein adsorption prevention function by means of an after-treatment.

Also, the present invention does not introduce phosphorylcholine groups by polymerizing phosphorylcholine-containing monomers onto the contact lens surface to coat it with a polymer different from the contact lens itself, as in a method described in Patent Document 4; it uses direct covalent bonding of phosphorylcholine groups, rather than polymer coating, and thus aims to achieve a superior protein adsorption prevention effect without changing the original characteristics of the contact lens with polymer coating.

Furthermore, the present invention aims to achieve a superior protein adsorption prevention effect by introducing a sufficient amount of phosphorylcholine, as opposed to the method described in Reference 5, which is shown to be incapable of introducing a sufficient amount of phosphorylcholine groups onto the contact lens surface when an attempt to duplicate this method is actually made.

Means to Solve the Problem

That is, the present invention provides a method of manufacturing an eye lens material having a process in which a phosphorylcholine group-containing chemical compound represented by the following formula (1) is reacted and covalently bonded to the surface of an eye lens material having hydroxyl groups wherein the chemical compound represented by the following formula (2) is reacted and covalently bonded through ester-bonding to the eye lens material in an organic solvent.

[Chemical formula 5]

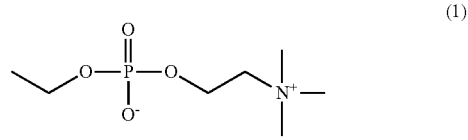

(1)

-continued

[Chemical formula 6]

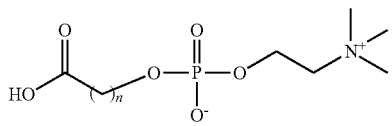
(2)

n denotes a natural number 1-18.

That is, the present invention provides a method of manufacturing an eye lens material having a process in which a phosphorylcholine group-containing chemical compound represented by the following formula (1) is reacted and covalently bonded to the surface of an eye lens material wherein hydroxyl groups are introduced to said eye lens material by means of a plasma treatment and then the chemical compound represented by the following formula (2) is reacted and covalently bonded through ester-bonding to the eye lens material in an organic solvent.

[Chemical formula 7]

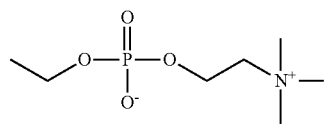
(1)

[Chemical formula 8]

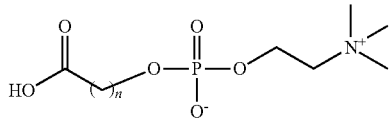
(2)

n denotes a natural number 1-18.

Furthermore, the present invention provides an eye lens material obtained by having the aforementioned phosphorylcholine group-containing chemical compound react, via a halogenated carboxylic acid derivative, with the hydroxyl groups on the eye lens material surface.

Also, the present invention provides a protein adsorption prevention method for an eye lens material wherein protein adsorption on the eye lens material is prevented by covalently bonding phosphorylcholine groups onto the eye lens material surface by means of an after-treatment in which the aforementioned phosphorylcholine group-containing chemical compound is reacted with the eye lens material.

Effects of the Invention

The manufacturing method of the present invention uses a simple after-treatment method to directly and covalently bond any amount of phosphorylcholine groups onto the eye lens material surface.

The eye lens material of the present invention is a contact lens onto whose surface phosphorylcholine groups are directly and covalently bonded and therefore it effectively suppresses protein adsorption on the contact lens and achieves a superior stain prevention effect. It can also improve moisture retention and the sensation of wearing [the contact lens].

Also, since the protein adsorption prevention function can be added by means of an after-treatment, the present invention can be easily used on existing contact lenses.

Since polymer coating is not used as the method to introduce the phosphorylcholine groups, durability is superior and the original characteristics of the contact lens are essentially not degraded.

The contact lens obtained by the present invention is a contact lens that gives a superior sensation when it is worn. Therefore it can be preferably used in situations where wearing contact lenses tends to feel like a foreign body [is touching the eye] due to reasons such as poor flexibility of the material.

The treatment method described in Patent Document 5 does not mention how to synthesize the phosphorylcholine group-containing chemical compound. Synthesizing it based on usual organic chemistry commonsense would end up in a very cumbersome and difficult process and there would be a shortcoming in that the yield would be low due to multiple steps.

Also, the reaction to introduce phosphorylcholine groups onto the contact lens surface, under the conditions described, does not proceed sufficiently and results in a low introduction level, which is insufficient for achieving a superior protein adsorption prevention effect.

In contrast, the after-treatment of the present invention has advantages in that it can introduce a sufficient amount of phosphorylcholine groups, it can achieve a superior protein adsorption prevention effect, and also it is a very practical method.

BRIEF DESCRIPTION OF DRAWINGS

FIG. 1 is a graph showing protein adsorption on a contact lens.

BEST MODE FOR CARRYING OUT THE INVENTION

The present invention is described in detail below.

"A method of preparing the phosphorylcholine group-containing chemical compound of formula (2)"

A phosphorylcholine group can be synthesized by means of total synthesis. However, the synthesis conditions are cumbersome, a strict moisture-free condition is required, and therefore the manufacturing cost is high.

On the other hand, phosphorylcholine can be extracted as lecithin, which is a constituent component of cell membranes; by removing the fatty acid portion by means of hydrolysis, [phosphorylcholine] can be easily obtained at low cost in the form of 1-α-glycerophosphorylcholine. The inventors discovered that a phosphorylcholine group-containing chemical compound can easily be obtained by means of oxidative cleavage of the diol portion of this 1-α-glycerophosphorylcholine.

The most representative synthesis method oxidizes 1-α-glycerophosphorylcholine by using sodium periodate and ruthenium trichloride in a solvent such as water and acetonitrile to obtain the target carboxyl derivative.

"An Eye Lens Material"

The eye lens material in the present invention refers to a molded piece of a material that is worn in the eye. It mainly refers to a contact lens.

A contact lens of any material can be used. The contact lens of the present invention can be prepared from a contact lens comprising a polymer such as methacrylic acid (MAA), acrylic acid (AA), 2-hydroxyethyl methacrylate (HEMA), N-vinylpyrrolidone (NVP), N,N-dimethylacrylamide (DMAA), vinyl alcohol (VA), methyl methacrylate (MMA), trifluoroethyl methacrylate (TFEMA), cellulose acetate butyrate (CAB), fluoro silicone, hexafluoroisopropyl methacrylate, perfluoroalkyl, methacrylate, siloxanyl methacrylate (SiMA), siloxanyl styrene (SiSt), ethylene glycol dimethacrylate (EGDMA), allyl methacrylate (AMA), and silicone macromers, as well as a copolymer of two or more types of monomers. The present invention is independent of the type of monomer, and it can be used for both hard contact lenses and soft contact lenses.

A soft contact lens that uses 2-hydroxyethyl methacrylate as the main constituent ingredient and an ionic soft contact lens prepared by copolymerizing it with methacrylic acid are representative soft contact lenses; these contact lenses are susceptible to protein adsorption. Therefore, they are preferably treated with the method of the present invention.

Also, a contact lens whose main or copolymerizing constituent monomer is vinyl alcohol is also treated preferably with the method of the present invention.

A contact lens that contains 2-hydroxyethyl methacrylate and/or polyvinyl alcohol as a functional group to which the phosphorylcholine group of the aforementioned formula (1) can covalently bond is preferable because it has hydroxyl groups.

However, even if these functional groups are not present, hydroxyl groups can be introduced by means of a plasma treatment. For example, hydroxyl groups can be introduced to a contact lens comprising N-vinyl pyrrolidone polymer to prepare the contact lens of the present invention. That is, hydroxyl groups are introduced onto the contact lens surface by using low temperature plasma in an oxygen gas atmosphere or oxygen/hydrogen gas atmosphere. Specifically, the contact lens is put into a plasma reactor vessel and, after a vacuum pump is used to form a vacuum in the reactor vessel, oxygen gas or oxygen/hydrogen gas is introduced. Hydroxyl groups can then be introduced onto the contact lens surface by means of glow discharge.

The phosphorylcholine group-containing chemical compound of formula (2) bonds covalently to the hydroxyl groups on the contact lens surface through ester bonding. As a result, a contact lens to whose surface the phosphorylcholine group of formula (1) is directly introduced through chemical bonding is obtained by the after-treatment of the contact lens.

The contact lens obtained by the present invention is different from lenses whose material is prepared by polymerizing phosphorylcholine group-containing monomers A lens coated with a phosphorylcholine group-containing polymer can suffer from peeling of the coating polymer and also is affected by the coating polymer.

"Preparation Method"

In the preparation method of the present invention, an ester bond is formed between the chemical compound of formula (2) and the hydroxyl group in the constituent monomer of the contact lens or the hydroxyl group newly introduced by means of a plasma treatment and such.

Specifically, the phosphorylcholine compound (2) is dissolved or suspended in an organic solvent such as dimethylsulfoxide, dimethylformamide, or tetrahydrofuran, and ester bonds with hydroxyl groups on the contact lens surface are formed by using a condensation agent such as carbonyldiimidazole, 1-ethyl-3-(3-dimethylaminopropyl) carbodiimide hydrochloride, thionyl chloride, phosphorus pentachloride, phosphorus oxychloride, phosphorus tribromide, or oxalyl chloride.

Of those listed above, thionyl chloride, phosphorus pentachloride, phosphorus oxychloride, phosphorus tribromide, or oxalyl chloride can be used to, via a halogenated carboxylic acid derivative, react with hydroxyl groups on the eye lens material surface. This method is preferable because the phosphorylcholine group introduction ratio can be controlled by controlling the equivalent weight of the reagent since good solubility results in a homogeneous solution to work with. Also, unlike a method in which phosphorylcholine groups are introduced by means of polymer coating, [this method] has very little influence on the contact lens itself, allowing it to maintain its basic performance as a lens.

A method that uses carbonyldiimidazole, 1-ethyl-3-(3-dimethylaminopropyl) carbodiimide hydrochloride and such for the condensation agent is inferior compared with the method of the present invention in terms of controlling the introduction ratio of the phosphorylcholine groups because the solubility of the active ester of the phosphorylcholine group[-containing] chemical compound is low in organic solvents.

"A Method of Preparing Carboxymethyl Phosphorylcholine by Means of the Oxidative Cleavage of 1-α-glycerophosphorylcholine"

For the chemical compound of formula (2), it is preferable to use carboxymethyl phosphorylcholine (n=1) obtained by the oxidative cleavage of 1-α-glycerophosphorylcholine.

1-α-glycerophosphorylcholine can be converted into carboxymethyl phosphorylcholine by means of the oxidative cleavage using periodate and ruthenium trichloride in a water/acetonitrile mixed solvent.

This reaction proceeds easily at room temperature; periodate in the amount of three equivalents or more of the amount of 1-α-glycerophosphorylcholine and a catalytic amount of the ruthenium compound (ruthenium trichloride, ruthenium tribromide, tris(acetylacetonat) ruthenium, etc. or hydrates thereof) are all that is required.

"A Method of Covalently Bonding the Phosphorylcholine Group of Formula (1) to the Hydroxyl Group of a Contact Lens"

A contact lens that contains 2-hydroxyethyl methacrylate and/or polyvinyl alcohol has hydroxyl groups. By reacting the carboxyl derivative of formula (2) with these hydroxyl groups, phosphorylcholine groups can be introduced onto the contact lens surface by means of ester bonding.

This reaction can easily proceed in an organic solvent such as dimethylformamide, dimethylsufoxide, tetrahydrofuran, and acetonitrile, in the presence of a carbodiimide type coupling agent such as carbonyldiimidazole and 1-ethyl-3-(3-dimethylaminopropyl) carbodiimide hydrochloride, or thionyl chloride, phosphorus pentachloride, phosphorus oxychloride, phosphorus tribromide, or oxalyl chloride.

The phosphorylcholine group of formula (1), introduced by means of the method described above or the like, is, after a pre-treatment using perchloric acid, quantified with the molybdenum blue method for quantitative analysis of phosphorus (Reference: 3.8.2 Phosphorus, Analysis, $4^{th}$ edition, Experimental Chemistry Course (14), Maruzen).

The amount of the phosphorylcholine group introduced onto the contact lens is preferably 0.0001 micromol/mg or more. If it is less than 0.0001 micromol/mg, then a sufficient protein adsorption suppression effect is not obtained sometimes; however, this does not apply to a case where the phosphorylcholine group is introduced only on the contact lens surface. The protein adsorption suppression effect increases as the amount introduced increases; therefore there is no upper limit for the amount introduced.

EXAMPLES

Next, the present invention is described in detail by referring to Examples. The present invention is not limited to these Examples.

"Synthesis of the Chemical Compound of Formula (2)"

5 g of 1-α-glycerophosphorylcholine was dissolved in water (70 ml)/acetonitrile (30 ml). As the temperature was lowered with ice, 17 g of sodium periodate and 80 mg of ruthenium trichloride were added, followed by overnight stirring. The precipitate was filtered, concentrated under a reduced pressure, and extracted with methanol to obtain 3.86 g (yield 82%) of the target carboxymethyl phosphorylcholine.

Carboxymethyl phosphorylcholine is the chemical compound of formula (2) for n=1.

"The Preparation Method of the Present Invention by Means of an After-treatment"

The chemical compound of formula (2) was used for an after-treatment of a commercially available contact lens and said chemical compound was ester-bonded to prepare a contact lens of the present invention.

"A Contact Lens Prepared by Ester-bonding the Chemical Compound of Formula (2), Via a Halogenated Carboxylic Acid Derivative, to Polymacon (Soft Contact Lens Medalist from Bausch & Lomb)"

10 mg of the chemical compound of formula (2) was added to 2 ml of dimethylformamide; 5 mg of thionyl chloride was then added, followed by 30 minutes of stirring. One piece of Polymacon, from which water had been removed by means of thorough substitution with dimethylformamide, was immersed in [this mixture] and 0.2 ml of triethylamine was added, followed by four hours of reaction time. The reaction solution was rinsed thoroughly with pure water to obtain a contact lens.

Example 2

A Contact Lens Prepared by Ester-bonding the Chemical Compound of Formula (2) to NelfilconA (Focus Dailies from Ciba Vision)

After removing water from NelfilconA by means of thorough substitution with dimethylsulfoxide, it was further immersed in 2 ml of dimethylsulfoxide, to which 10 mg of the chemical compound of formula (2) and 7 mg of 1-ethyl-3-(3-dimethylaminopropyl)carbodiimide hydrochloride were added, followed by six hours of reaction time. The reaction solution was rinsed thoroughly with pure water to obtain a contact lens.

Example 3

A Contact Lens Prepared by Ester-bonding the Chemical Compound of Formula (2) to NelfilconA (Soft Contact Lens Medalist from Bausch & Lomb).

After thoroughly substituting dimethylsulfoxide for water contained in Polymacon, it was immersed in 3 ml of dimethylsulfoxide. 10 mg of carboxymethyl phosphorylcholine, 6 mg of carbonyldiimidazole, and 10 mg of triethylamine were added, followed by 12 hours of reaction time at 25° C. The contact lens was thoroughly rinsed with dimethylsulfoxide and then with water to obtain the target contact lens. The phosphorus quantification showed the introduced phosphorylcholine level as 0.817 micromol/mg.

Example 4

A Contact Lens Prepared by Ester-bonding the Chemical Compound of Formula (2) to NelfilconA (Focus Dailies from Ciba Vision)

After thoroughly substituting dimethylformamide for water contained in NelfilconA, it was immersed in 3 ml of dimethylformamide. 10 mg of carboxymethyl phosphorylcholine, 10 mg of dicyclohexylcarbodiimide, 10 mg of hydroxybenzotriazole, and 10 mg of triethylamine were added, followed by 12 hours of reaction time at 25° C. The contact lens was thoroughly rinsed with dimethylsulfoxide and then with water to obtain the target contact lens. The phosphorus quantification showed the introduced phosphorylcholine level as 0.165 micromol/mg.

The phosphorylcholine group of formula (1) introduced by covalent bonding was quantified in the following manner.

<Quantification Method>

The obtained contact lens was immersed in perchloric acid and heated up to 180° C. to be decomposed. The obtained solution was diluted with water, to which hexaammonium heptamolybdate tetrahydrate and L-ascorbic acid were added, followed by 5 minutes at 95° C. of color development time; the amount introduced was determined by means of the light absorption measurement at 710 nm. For the calibration curve, a sodium dihydrogen phosphate solution was used.

Comparative Example 1

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. Polymacon, which was used in Example 1, was immersed in this solution, followed by 12 hours of reaction time at room temperature. The contact lens was thoroughly rinsed with dimethylsulfoxide and then with water; the phosphorus quantification showed the level of the introduced phosphorylcholine group to be the detection limit, 0.0001 micromol/mg, or less, indicating that the reaction did not proceed.

Comparative Example 2

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. NelfilconA, which was used in Example 2, was immersed in this solution, followed by 12 hours of reaction time at room temperature. The contact lens was thoroughly rinsed with dimethylsulfoxide and then with water; the phosphorus quantification showed the level of the introduced phosphorylcholine group to be the detection limit, 0.0001 micromol/mg, or less, indicating that the reaction did not proceed.

"Protein Adsorption Experiment"

The protein adsorption suppression effect was compared for Examples 1 and 2, Comparative examples 1 and 2, and commercially available soft contact lenses (Comparative examples 3-7) by using the following evaluation method.

Comparative Example 3

EtafilconA (product name: 1-Day Acuvue from J & J)

Comparative Example 4

EtafilconA (product name: 1 Day Aquair from Ocular Science)

Comparative Example 5

NelfilconA (Focus Dailies from Ciba Vision)

Comparative Example 6

Polymacon (product name: Medalist from Bausch & Lomb)

Comparative Example 7

VifilconA (Focus from Ciba Vision)
"Evaluation Method"

A contact lens was immersed in 3 ml of an artificial lacrimal fluid and left alone for 24 hours at 37° C. The protein level in the solution portion was quantified with the BCA method (the calibration curve: Albumin Bovine); the protein adsorption level was determined as the reduction in the proteins in the solution portion.

The artificial lacrimal fluid was obtained by dissolving the following ingredients in ultra pure water:
1.20 mg/ml lysozyme, 3.88 mg/ml albumin, 1.61 mg/ml γ-globulin, 9.00 mg/ml sodium chloride, 0.14 mg potassium dihydrogen phosphate, and 0.80 mg/ml disodium hydrogen phosphate heptahydrate. (Reference) FDA Guideline Draft: Testing guidelines for class III soft (hydrophilic) contact lens solution, lens group compatibility test. Jul. 15, 1985.

FIG. 1 shows the results of protein adsorption for Examples 1 and 2 and Comparative examples 1-7. These results indicate that the contact lenses of the present invention significantly suppress protein adsorption.

Industrial Applicability

The present invention can highly suppress protein adsorption on contact lenses and significantly prevent stains due to proteins.

The manufacturing method of the present invention can be preferably used for soft contact lenses, for which protein staining is a fatal problem. It can be preferably used in particular for ionic soft contact lenses, which accelerate protein adsorption.

It can also be preferably used for hard contact lenses for sustained wearing and/or with oxygen permeability, to which proteins tend to be adsorbed.

The invention claimed is:

1. A method of after treating an ionic soft contact eye lens which accelerates protein adsorption, or a hard contact eye lens for sustained wearing and/or with oxygen permeability to which proteins tend to be adsorbed, whereby to prevent protein adsorption, comprising:

obtaining by oxidative cleavage of 1-α-glycerophosphorylcholine using periodate and ruthenium trichloride in a water/acetonitrile mixed solvent, carboxymethyl phosphorylcholine represented by the following formula (2):

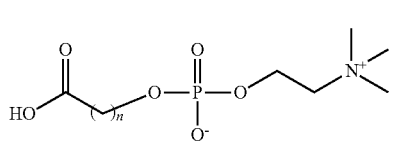

Chemical formula 2 wherein n=1; and reacting and covalently bonding through ester-bonding to said eye lens, said carboxymethyl phosphorylcholine in an organic solvent.

2. A method of after treating an ionic soft contact eye lens which accelerates protein adsorption, or a hard contact eye lens for sustained wearing and/or with oxygen permeability to which proteins tend to be adsorbed, whereby to prevent protein adsorption, comprising:

obtaining by oxidative cleavage of 1-α-glyeerophosphoryleholine using periodate and ruthenium trichloride in a water/acetonitrile mixed solvent, carboxymethyl phosphoryleholine represented by the following formula (2):

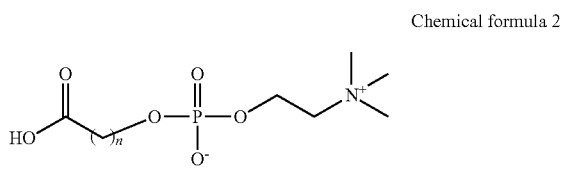

Chemical formula 2 wherein n=1;

introducing hydroxyl groups to said eye lens by means of a plasma treatment; and reacting and covalently bonding, through ester-bonding to said eye lens having hydroxyl groups, said carboxymethyl phosphoryleholine in an organic solvent.

* * * * *